United States Patent
Smith

(10) Patent No.: US 10,445,591 B2
(45) Date of Patent: Oct. 15, 2019

(54) AUTOMATED TARGET RECOGNITION BASED BODY SCANNER USING DATABASE SCANS

(71) Applicant: Steven Winn Smith, San Diego, CA (US)

(72) Inventor: Steven Winn Smith, San Diego, CA (US)

(73) Assignee: TEK84 ENGINEERING GROUP, LLC, San Diego, CA (US)

( * ) Notice: Subject to any disclaimer, the term of this patent is extended or adjusted under 35 U.S.C. 154(b) by 65 days.

(21) Appl. No.: 15/726,244

(22) Filed: Oct. 5, 2017

(65) Prior Publication Data

US 2019/0108403 A1    Apr. 11, 2019

(51) Int. Cl.

| | |
|---|---|
| *G06K 9/00* | (2006.01) |
| *G06K 9/78* | (2006.01) |
| *G06K 9/46* | (2006.01) |
| *G06K 9/20* | (2006.01) |
| *G06K 9/62* | (2006.01) |
| *G06F 16/583* | (2019.01) |
| *G06F 19/00* | (2018.01) |

(52) U.S. Cl.
CPC ..... *G06K 9/00771* (2013.01); *G06K 9/00369* (2013.01); *G06K 9/209* (2013.01); *G06K 9/4604* (2013.01); *G06K 9/6202* (2013.01); *G06K 9/78* (2013.01); *G06F 16/5854* (2019.01); *G06F 19/321* (2013.01); *G06K 2209/21* (2013.01)

(58) Field of Classification Search
None
See application file for complete search history.

(56) References Cited

U.S. PATENT DOCUMENTS

| | | |
|---|---|---|
| 5,133,020 A | 7/1992 | Giger et al. |
| 5,181,234 A | 1/1993 | Smith |
| 7,426,287 B2 | 9/2008 | Yoon et al. |
| 7,805,001 B2 | 9/2010 | Volkau et al. |
| 8,494,297 B2 | 7/2013 | Zhang et al. |
| 2009/0196481 A1 | 8/2009 | Li et al. |
| 2015/0339521 A1* | 11/2015 | Chen .................. A61B 5/0064 382/103 |

* cited by examiner

*Primary Examiner* — Idowu O Osifade
(74) *Attorney, Agent, or Firm* — Sheppard, Mullin, Richter & Hampton LLP

(57) ABSTRACT

Body scanners are used in airports and other secured facilities to detect weapons, explosives, and other security threats hidden under persons' clothing. These devices use x-rays, millimeter waves and other radiant energy to produce an electronic image of the person's body and any concealed objects. Examination of these images by human analysts is slow, expensive, and subject to privacy concerns. The Invention provides automated analysis by comparing each image against a database of previous scans, using a plurality of subjects with different body types. This comparison is facilitated by digitally mapping each body scanner image to humanoid coordinates. This overcomes the failings of the prior art by allowing each anatomic location on one person to be referenced to the same anatomic location on all other persons.

18 Claims, 7 Drawing Sheets

30 PRIOR ART  31 FIG. 2  32

AUTOMATED TARGET RECOGNITION BASED BODY SCANNER USING DATABASE SCANS

This application claims the benefit of provisional patent application No. 62/406,702 filed with the USPTO on Oct. 11, 2016, with the same title and inventor.

BACKGROUND OF THE INVENTION

This invention relates to screening persons for security threats through the automated analysis of body scanner images.

A variety of body scanners have been developed to detect weapons, explosives and contraband concealed under the clothing of persons entering security controlled areas. These devices operate by detecting radiant energy that has been modulated by or emitted from the body of the person being examined. Radiant energies used include: x-rays, microwaves, millimeter waves, infrared light, terahertz waves, and ultrasound. In a typical operation, the person being examined is actively exposed to a beam of millimeter waves or x-rays. A portion of this radiant energy interacts with the person, their clothing, and any concealed objects they may be carrying. This interaction modulates the radiant energy reflected from, scattered by, or transmitted through the person. This reflected, scattered or transmitted radiant energy is collected by sensitive detectors, and the resulting electronic signals are routed to a digital computer. Alternatively, some body scanners operate passively, collecting radiant energy that has been thermally emitted from the person's body and surrounding area. Examples of this are infrared and millimeter wave sensitive cameras. Regardless of active or passive operation, body scanners convert the electronic signals from their detectors into digitally represented images of the person's body. In these images the clothing is essentially transparent, allowing the security officer to visualize objects that are concealed underneath the clothing. Commercial body scanners include the model AIT84, sold by Tek84 Engineering Group, San Diego, Calif.; model SECURE 1000, sold by Rapiscan Security Products, Torrance, Calif.; model SmartCheck, sold by American Science and Engineering, Billerica, Mass.; model ProVision, sold by L-3 Communications, Woburn, Mass.; and model Eqo, sold by Smiths Detection, Edgewood, Md.

FIG. 1 shows examples of the wide variety of body scanner configurations. In one configuration 100, the person being screened 12 stands motionless within the apparatus 101 performing the scan. In another configuration 102, the person 12 stands next to the scanning device 103. In yet another configuration 104, the person 12 walks along a path 20 through an archway body scanner 105. Many other configurations are possible, including: cameras detecting infrared or microwave energy, the person being screened turning their body in front of a scanning panel, and standoff systems where the person is scanned from a considerable distance from the apparatus. Examples of body scanner images are shown in FIG. 2, created from backscatter x-rays 30, transmitted x-rays 31, and passive microwaves 32.

In spite of using different radiant energies and imaging geometries, body scanners detect concealed objects in the same fundamental way: they create an electronic image of the person with the clothing being essentially transparent. This electronic image is composed of bits of digital information, which may reside in a storage medium, computer processing unit, or other device capable of retaining such data. For image storage this may be done in a common file format, such as jpg, bmp, or gif. Within a computer processing unit the storage will typically be pixel values ordered in a row and column arrangement. The electronic image can be manipulated directly in digital form, or converted to a visual image by devices such as image printers and video monitors. As used here, and commonly in the art, the term "image" and "scan" refer to the bits of digital information residing in a digital device, the visual display of this information on a video monitor, the printed image corresponding to this digital information, and other such data presentations. These concepts of digitally representing and manipulating images are well known in the art of image processing.

All body scanners incorporate a digital computer, as shown in FIG. 1 18 that receives or otherwise acquires an electronic image from the imaging assemblies. In the most basic operation, this electronic image is displayed on a monitor 16, either mounted directly on the scanning apparatus or located in close proximity. The security officer 14 evaluates the displayed image through his innate and trained ability to recognize the normal visual appearance of the human body. That is, the security officer knows what the human body looks like and can therefore detect objects appearing in the displayed image that do not correspond to human anatomy. In addition, from his training and experience in society, the security officer can often recognize which of the concealed objects are benign and need no investigation, such as wallets, watches, coins, buttons on the clothing, and so on. If the security officer observes an object that is not a part of the subject's body, and is not recognized as benign, the security officer confronts the subject to determine if the object is a prohibited item. This may be as simple as asking the subject to remove the item from within their clothing, or as invasive as a strip search. The method of resolution depending on the characteristics of the object observed and the policies of the security facility being entered.

Body scanners are capable of detecting a wide range of security threats and contraband; however, the required image interpretation by the Security Officer presents a multitude of problems and difficulties. The manpower requirement to operate these systems is very high, requiring a security officer to be present to analyze each image. This is aggravated by the specialized training each security officer must go through to be proficient in the image analysis. The inherent limitations of human image analysis, and the nature of this work, promotes errors and deficiencies in the security screening process. For instance, security officers may become distracted or tired and miss concealed objects. In a worse scenario, a security officer may be bribed or coerced to ignore concealed objects. Further, human image analysis requires that the examination area be large enough to accommodate the extra security officer. Further, humans require about ten seconds to process each image, which can slow the throughput of the security checkpoint. Still further, some persons object to an electronic image of their unclothed body being displayed and viewed by the security officer.

FIG. 3 illustrates a configuration directed at overcoming these problems of operator image interpretation, commonly know as "Automated Target Recognition," or ATR. In this approach the human operator is replaced by a digital computer running specialized software 90. The electronic image 70 produced by the body scanner contains a digital representation of the person's body 71, as well as any concealed objects 72, 73. This digital information 74 is passed into the digital computer 90. This may be the computer operating the body scanner, as shown in FIG. 1 18, or a separate device connected to the apparatus through a communication network. The goal of ATR software is to discriminate between features in the image that correspond to the person's anatomy 71, and features that correspond to concealed objects 72, 73. The result of this operation is digital data 84 representing only the concealed objects, and not the human body. The Security Officer operating the body scanner is then notified of this information 84 through an annunciator in some convenient way. Most commonly, this is done through a graphical representation 80 displayed on the system's monitor 18. A cartoon-like outline 81 may be used to provide positional reference. However, this outline 81 is the same for all persons being scanned, and does not correspond to the anatomy 71 of the particular human body being examined. Also most commonly, concealed objects 72 73 in the electronic image 70 are displayed to the operator as boxes 82 83, respectively, or some other pattern in the graphical display 80. An additional problem in ATR is the presence of common benign objects that cannot easily be divested from the person being screened. This includes jewelry, zippers, buttons and the like. It is highly desirable or necessary to allow these objects to remain on the person during the body scan.

The performance of ATR can be statistically measured in terms of the probability of detecting certain types of concealed objects, versus the false alarm rate. A well performing system detects a high percentage of the concealed objects with minimal false alarms. Conversely, a poorly performing system has a low detection probability, and a high false alarm rate. Humans perform exceedingly well at this task with a seemingly trivial effort. This can be appreciated simply by looking at the high-quality body scan image 70 in FIG. 3. The human brain can immediately separate the person's body from the concealed objects. In stark comparison, prior art ATR has surprisingly poor performance at this task. While the numbers are arguable, in can generally be said that the capability of prior art ATR is orders-of-magnitude below that of human image interpretation. The reasons for this have not been known; it has been a longstanding and frustrating mystery to the scientists and engineers working in the field.

Prior Art approaches generally employ one of two strategies for ATR. The first uses reference information that is contained within the image being examined. One such scenario is described in U.S. Pat. No. 8,194,822, to Rothschild et al., issued Sep. 28, 2010. In this '822 Invention, the value of a particular pixel is compared against a plurality of other pixels values in the same image, providing a reference to detect uncommonly bright or dark areas. Another Invention using this first general strategy is described in U.S. patent application Ser. No. 62/406,702, to Smith, filed Oct. 11, 2016, and incorporated herein by reference. In this Invention, an image feature at one location in the image is compared to the bilateral location in the same image, thereby detecting features that are bilaterally symmetric. In general, human anatomy is bilaterally symmetric, while concealed threats are bilaterally asymmetric. Therefore, this provides a method for separating anatomic from threat features, by only using information contained within the single scanned image.

The second general approach to ATR is to use reference information in a library, i.e., a database, of previously acquired scans. This strategy is described in U.S. Pat. No. 5,181,234, to Smith, issued May 22, 1991, and incorporated herein by reference. In the '234 Invention, a plurality of body scanner images is acquired and analyzed for the presence of image features. These features are stored in a library for later comparison to scans of actual subjects. Features appearing in the actual scans, which do not appear in the library, are classified as potential threats. As briefly stated in the '234 patent: "The location of detected features can be referenced to the absolute location in the image, or in relation to the body of the person being examined" (col. 14 lines 41-43). However, '234 is silent on how a location "in relation to the body" can be calculated or otherwise determined.

Inadequate ATR has placed severe limitations on the use of body scanners. Security personnel at airports, military bases and Government facilities have been faced with undesirable alternatives. One alternative is to use body scanners with human image analysts, providing excellent detection capability and few false alarms. However, they also must accept the associated manpower problems, long analysis times, and privacy concerns. The other alternative has been to use body scanners with prior art ATR. This provides high-throughput, reduced personnel requirements and far better privacy to the person being screened. However, in this alternative, the primary purpose of the body scanner is largely defeated, a result of the poor detection probability and frequency false alarms. A third alternative, which is often selected, is to not use body scanners because of the unacceptable problems of either using, and not using, prior art ATR. Indeed, the performance of ATR is the critical factor in the widespread use of body scanners in security facilities.

BRIEF SUMMARY OF THE INVENTION

The Present Invention provides body scanner automation by comparing the scanned image against a database of previously scanned images in a common spatial frame-of-reference matched to the human body, referred to as humanoid coordinates. These humanoid coordinates enable each feature in the scanned image to be classified according to how common it is in the general population of persons being scanned. Features that are common are ignored. Features that are uncommon are suggestive of a threat object being present, and subjected to further scrutiny.

In one preferred embodiment, a body scanner is used to acquire a database of scanned images, representative of the general population of persons that may be searched. A computer algorithm converts the images in this database from the spatial coordinates produced by the scanner to humanoid coordinates. The goal and purpose of the humanoid coordinates is to align the body parts appearing in each of the images. That is, the arms, head, torso, legs and feet in any one image are spatially aligned with the arms, head, torso, legs and feet in all of the images. Subsequently, the body scanner is used to acquire a scanned image of a subject that is being screened for the presence of concealed threats. This subject image is also converted to humanoid coordinates. Image features are identified in the subject scan, such as the brightness of an area, the strength of an image edge, the angle of an image edge, a measure of the image texture, detection of geometric shapes such as corners, or other characteristics known to those in the field of digital image processing. Each of these features appearing in the subject scan is evaluated for its frequency of occurrence in the database scans. This is accomplished by searching each image in the database for the presence or absence of the indicated feature, at the same location in humanoid coordinates that the feature appears in the subject scan. Image features in the subject scan that appear commonly in the database scans are classified as normal and discarded from further consideration. Conversely, image features in the subject scan that do not appear in the database scans, or only infrequently occur, are classified as abnormal or suspicious, and further evaluated. In another preferred embodiment, the database scans are consolidated into a statistical representation to facilitate their comparison to the subject scan.

It is therefore a goal of the Present Invention to provide an improved method and apparatus for detecting security threats concealed under the clothing of persons entering a security controlled area. Another goal of the Present Invention is to provide improved ATR capability for body scanners. Yet another goal is to use the information embedded in a database of scans to represent the characteristics of the general population that may be searched with the body scanner. Still another goal is to facilitate the comparison of body scanner images through a humanoid coordinate system. A further goal is to provide ATR discrimination based on the probability of occurrence of features in the scanned image. Yet another goal is to eliminate the need for humans to view and analyze body scanner images.

DETAILED DESCRIPTION OF THE INVENTION

Figure 1:
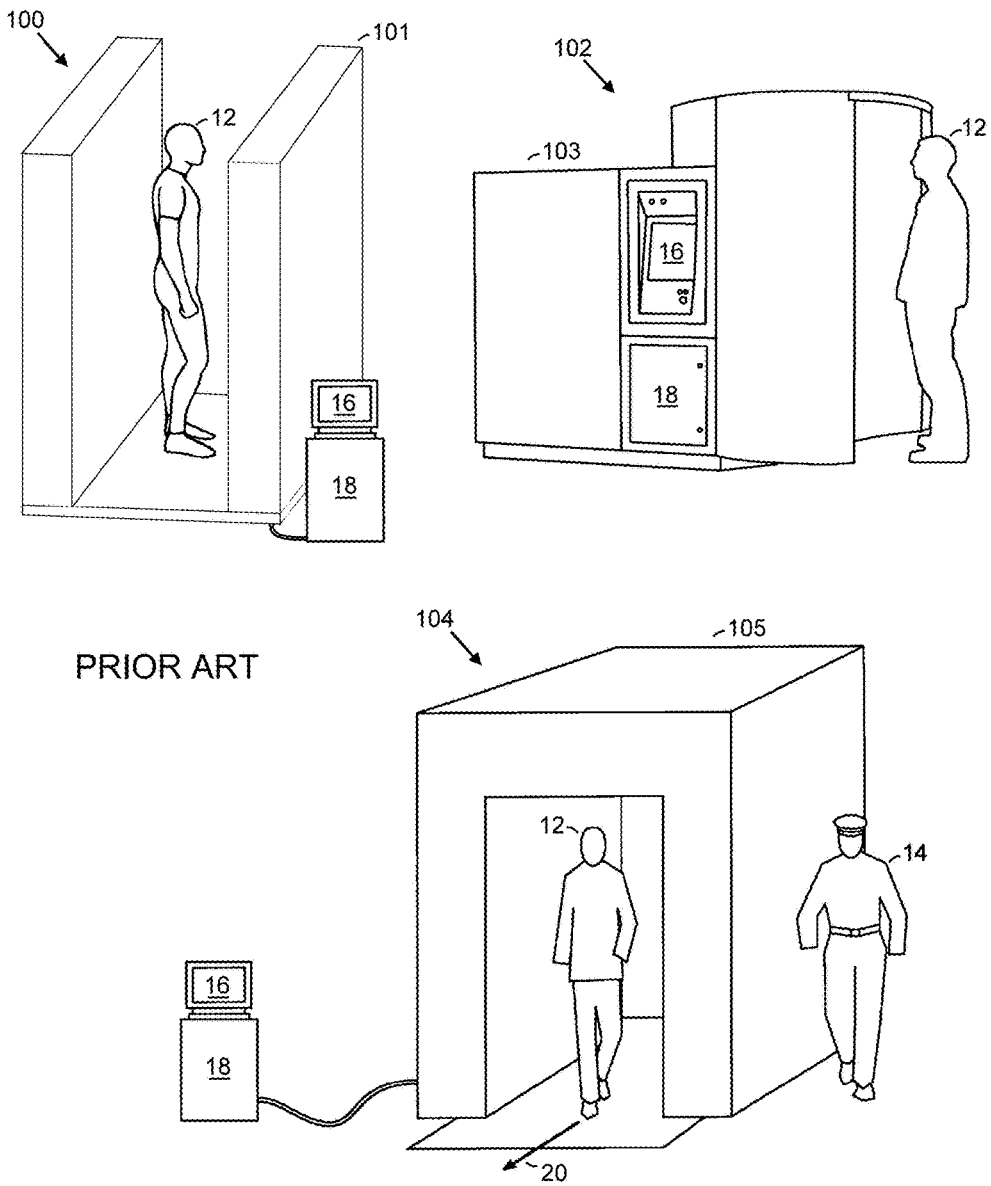
FIG. 1 is a depiction of the prior art.
Figure 2:
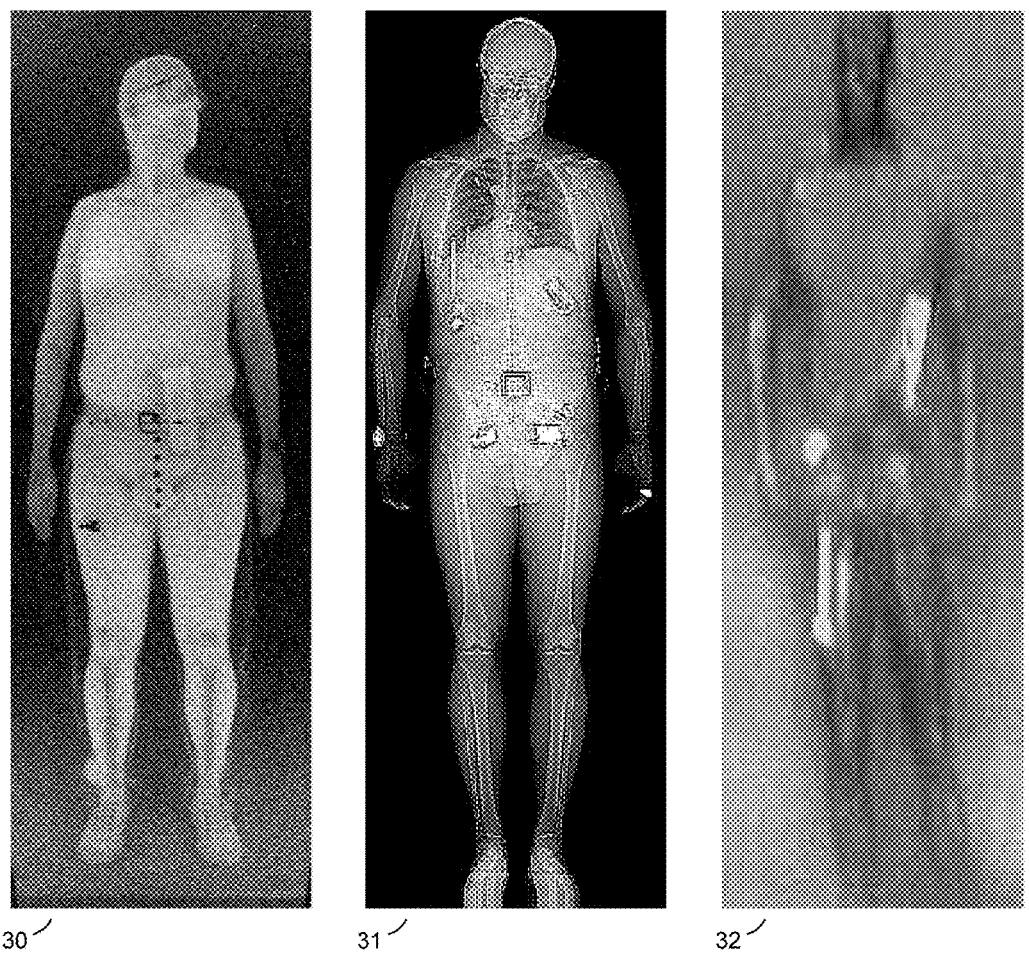
FIG. 2 is a depiction of the prior art.
Figure 3:
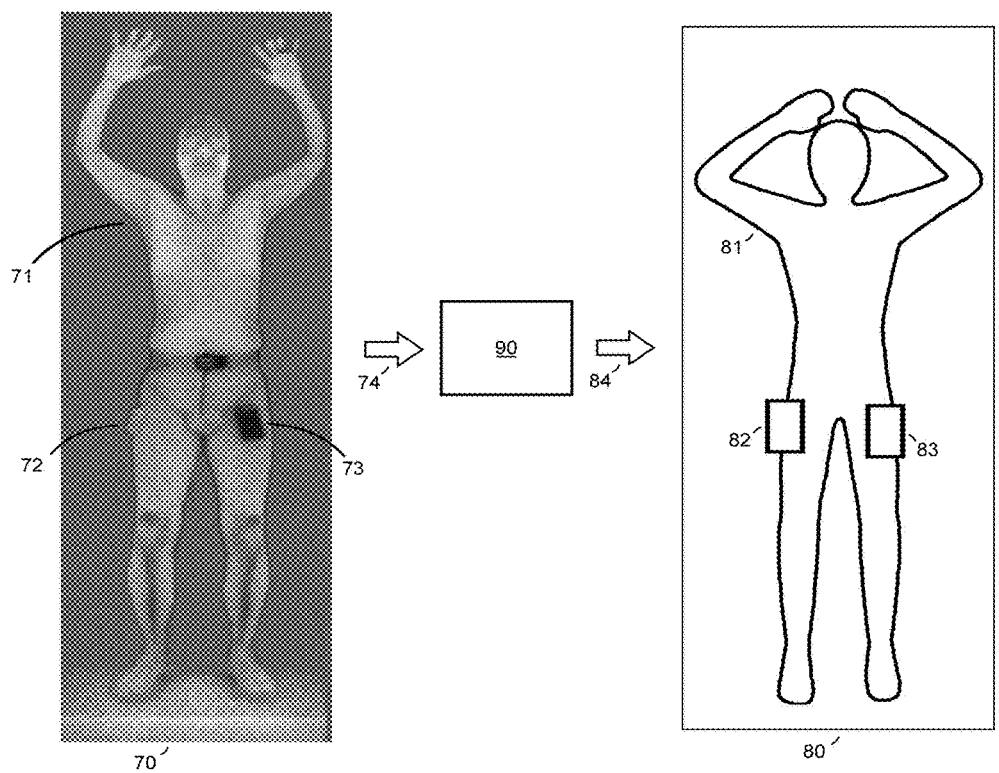
FIG. 3 is a depiction in accordance with the Present Invention.
Figure 4:
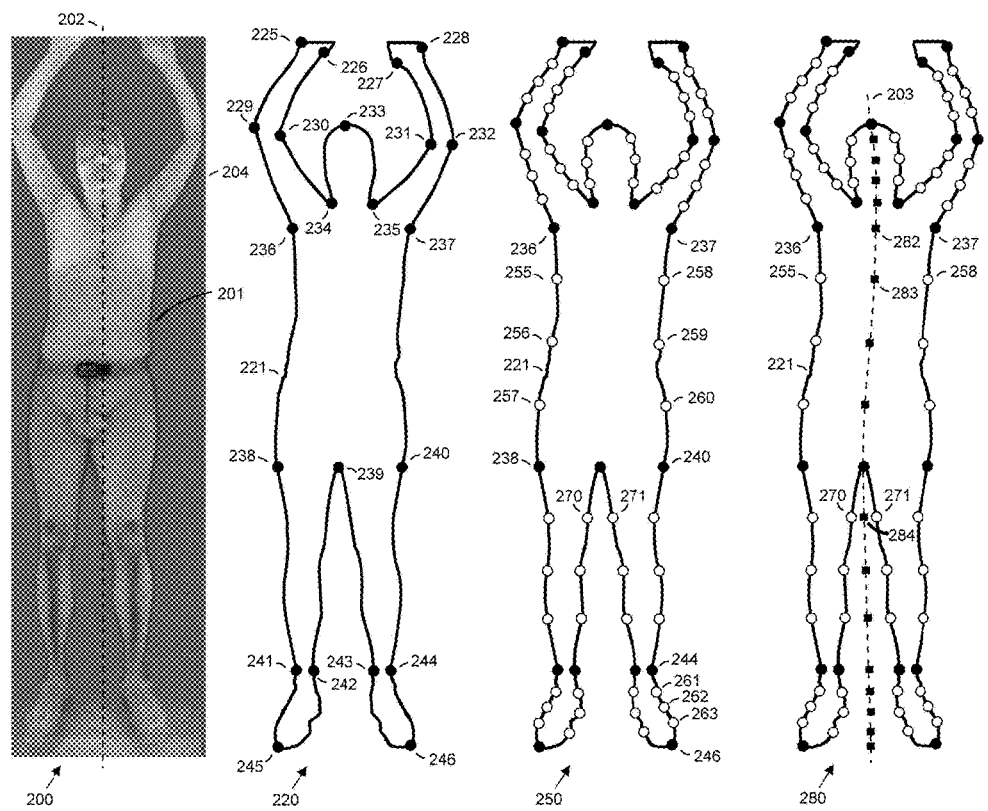
FIG. 4 is a depiction in accordance with the Present Invention.

FIGS. 4 through 7 are useful to describe the general operation of the Present Invention, as well as a preferred embodiment. The leftmost FIG. 200 in FIG. 4 shows an image 204 produced by a body scanner, along with the vertical centerline 202 of the image. As can be seen, the displayed body 201 is generally symmetrical between its left and right sides, but the line of symmetry deviates from the centerline 202 of the image. FIG. 4 also shows illustrations of three sequential computer processing steps 220 250 280. The outline 221 of the body 201 is first generated. The algorithms for performing this step are well known in the art of digital image processing, such as thresholding, edge detection and morphological operations. The exact nature of this step depends on the characteristics of the particular type of body scanner being used. In a preferred embodiment, the electronic image 204 comprises backscatter and transmission images, such as produced by the previously mentioned AIT84 and SmartCheck products. In this embodiment the outline 221 of the body can be obtained by thresholding the transmission image to generate a silhouette of the body, followed by an edge detection routine. In any event, the types of operations and techniques to generate the body outline 221 from the body 201 are well known in the art. The resulting outline 221 may be represented by pixel values in a digital image, a mathematical equation, or other way of specifying the location of the body edge. In the preferred embodiment, the outline 221 consists of pixel values in a digital image with about four times the spatial resolution of the original image 204. For example, if the original digital image 204 is composed of 150 by 600 pixels, the outline data 220 would be an image of 600 by 2,400 pixels, thereby providing subpixel localization of the body edge. The data sets of the subsequent operations 250 280 have this same preferred representation.

In a second step, the primary fiducial markers 225-246 are identified on the outline 221. These are located through common image processing algorithms looking for specific image features. In a preferred embodiment, the wrists 225 226 227 228 and ankles 241 242 243 244 are defined by locating the narrowest point across the limb. The inside and outside of the elbows 229 230 231 232, and the tips of the feet 245 246 are identifiable by the abrupt change in slope of the outline 221. The neck 234 235 and groin 239 are readily located as the lowest and highest points in the local region, respectively. The armpits 236 237 are determined by starting at the neck fiducials 234 235, respectively, and moving outward and down until intersecting the outline 221. Likewise, the hip fiducials 238 240 are at the location on the outline 221 with the same height as the groin 239. The top of the head 233 is located by finding the best-fit circle matching the top of the head, then constructing a line between the center of this circle and the midpoint between the neck fiducials 234 235. The top of the head 233 is then identified as the point where this line intersects the outline 221. Algorithms to carry out these steps are routinely known in digital image processing, have many variations, and are tailored to the particular type of body scanner being used.

The third step shown in FIG. 4 is to locate a large number of secondary fiducial markers 255-263 from the location of the primary fiducial markers 225-246 and the body outline 221. This operation will be explained by using the primary fiducials in the armpit 236 and hip 238 as an example. The path of the body outline is traced from the armpit 236 to the hip 238. This path-length is divided into fourths, providing the location of three secondary fiducials 255 256 257. Likewise, on the other side of the body, the path-length between primary fiducials at the armpit 237 and hip 240 is divided into fourths, to locate three additional secondary fiducials 258 259 260. Another example shown of this is the primary fiducials for ankle 244 and toe 246 being used to locate additional secondary fiducials 261 262 263. This operation is carried out on all adjacent primary fiducials in the image, in the same manner as in these three examples. This description breaks each path-length into fourths; however, this is only for simplicity of explanation. In a preferred embodiment, the path length between adjacent primary fiducials is broken into several hundred segments, providing the location of several hundred secondary fiducials. This makes the distance between adjacent secondary fiducials smaller than the pixel spacing of the electronic image that is representing this data. That is, the totality of the primary and secondary fiducials trace the body outline 221 to subpixel accuracy. In some of the following steps there is no distinction between primary and secondary fiducials, and they are referred to jointly as "fiducials."

A key feature of this multitude of fiducials is that they occur in bilateral pairs. For example, the two armpit fiducials 236 237 form such a pair. As shown in the data representation 280, the midpoint 282 between these fiducials 236 237 is located on the body's axis of symmetry 203 of the body outline 221. Likewise fiducials 255 and 258 form a pair around midpoint 283, and fiducials 270 271 form a pair around midpoint 284. Put in other words, the vertical axis of symmetry 203 of the body outline 221 can be calculated as all of the midpoint locations [e.g., 282 283 284] of all the pairs [e.g., 236 and 237, 255 and 258, 270 and 271, respectively].

Figure 5:
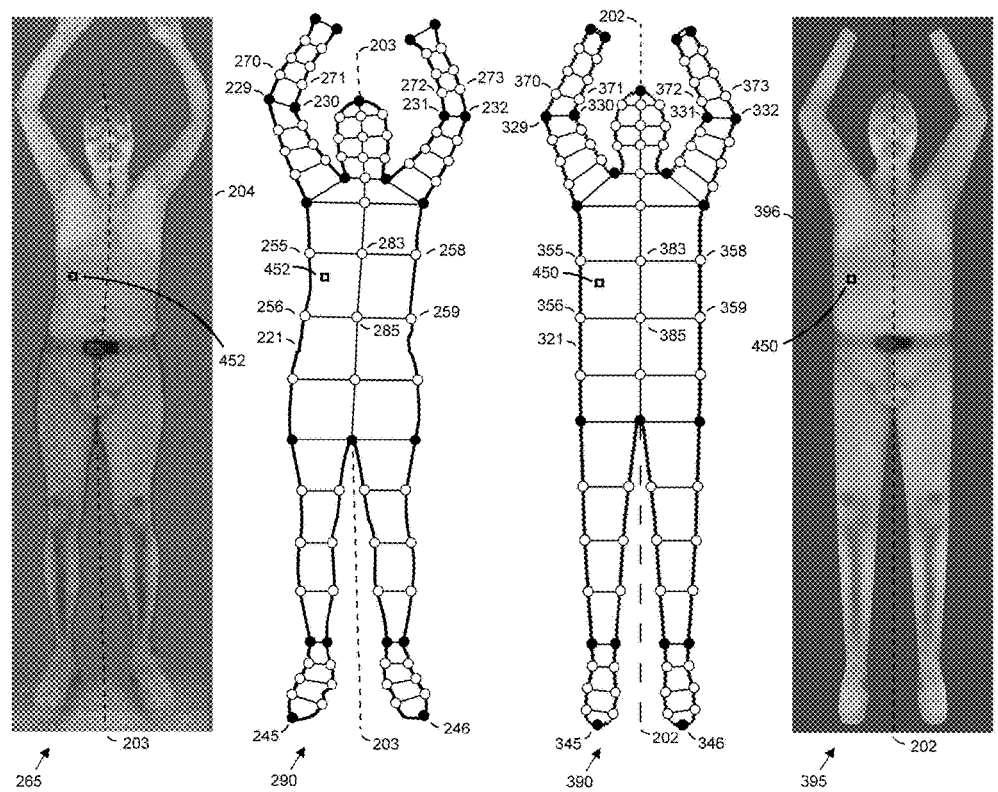
FIG. 5 is a depiction in accordance with the Present Invention.

The Present Invention is based on conversion from the scanned image coordinates to humanoid coordinates. FIG. 5 is useful in explaining this process and shows a preferred embodiment, continuing from the concepts presented in FIG. 4. The leftmost FIG. 265 in FIG. 5 shows the acquired image 204 with the body axis of symmetry 203 identified, as previously described. FIG. 5 shows three additional illustrations 290 390 395 that describe image warping, a well-known technique in the art of image processing. The original electronic image 204 is characterized by a multitude of fiducials connected to form a mesh of quadrilaterals over the image 290. Each of the fiducials is shifted to a new location 390, thereby warping the mesh of quadrilaterals into a new spatial coordinate system. To complete the process, the bilinear transform, or similar, is used to map the grayscale values in the original electronic image 204 to their corresponding locations in the humanoid coordinate image 396.

This new spatial coordinate system, referred to as humanoid coordinates, is based on the characteristics of the human body, thereby facilitating the comparison of images of the human body. It is a fixed, single, common coordinate system for all scanner images involved in the Present Invention. In the preferred embodiment of the Present Invention it is formatted to resemble a simplified outline of the human body. That is, every image generated from the body scanner will be unique in its grayscale representation, body outline, and fiducials, as typified in FIG. 5 265 290. However, after any image is converted to humanoid coordinates, the outline of the body and fiducials, as typified in FIG. 5 390, will be the same. That is, there is only one body outline and one set of fiducials in humanoid coordinates, regardless of the particular image being processed. The rightmost figure in FIG. 5 395 shows the corresponding grayscale information 396 that results from the original image 204 undergoing this coordinate transform. The outline of the body is the same as the outline 321 of the wireframe 390; however, the grayscale in this image 396 is uniquely derived from the original image 204.

The purpose and goal of this coordinate conversion is to spatially align all scanner images with each other, allowing a comparison among them. Without this coordinate conversion it is difficult or impossible to compare any two images, much less a multitude of images, because of the infinite variation in body shapes and postures. Accordingly, the specific characteristics of the humanoid coordinates are not important; only that the process is the same for all images, and the humanoid coordinates generally resemble the human body. It is within the scope of the Present Invention that the humanoid coordinates could be as diverse as tabulated data in a spreadsheet, to rectangular body outlines in an image format, to formats derived from known techniques such as principle component analysis.

In further detail, the body outline with fiducials 290 is calculated by finding the outline of the body, locating key landmarks on the body as primary fiducials, inserting a selected number of secondary fiducials between the primary fiducials, and connecting the corresponding fiducials to form quadrilaterals. In the humanoid coordinates this procedure also defines a body outline with fiducials 390, with a one-to-one correspondence to the original image 290. That is, the exemplary fiducials in the scanned coordinates 270-273 correspond to fiducials 370-373, respectively, in the humanoid coordinate frame. Likewise, fiducials 229-232 correspond with fiducials 329-332 and fiducials 255 283 258 256 285 259 245 246 correspond to 355 383 358 356 385 359 345 346, respectively. The exemplary quadrilateral defined by fiducials 272 273 232 231 thereby corresponding to the quadrilateral defined by fiducials 372 373 332 331.

The bilinear transform, a mathematical mapping technique known in the field of digital image processing, maps the location of each point within one quadrilateral into a corresponding location in a second quadrilateral. In a preferred embodiment, a computer routine loops through each of the pixel locations in the humanoid coordinate image 396. In FIG. 5 one such exemplary pixel location is identified 450. The four quadrilateral corner locations that contain this pixel location in humanoid coordinates are identified 355 383 385 356. The bilinear transform is then used to calculate the corresponding location 452 in scanner coordinates, using the corresponding quadrilateral corner locations 255 283 285 256. Finally, the grayscale value at these scanner coordinates 452 is transferred to the grayscale value at the humanoid coordinates 450. In this manner, the grayscale image 396 in humanoid coordinates can be calculated from the original scanned image 204. This bilinear mapping procedure is well known in the art of image processing, and is provided as a standard function in many image processing toolkits, such as Matlab. Many variations are possible that accomplish the same result, all known in the art. These include breaking each of the quadrilaterals into two triangles, and then applying an Afine transform. Alternatively, the quadrilaterals can be broken into lines, and warped by a line-by-line mapping algorithm. While these techniques for mapping one small region into another small region, such as the bilinear transform, are known in the art, the determination of the fiducial locations that define these small regions is unique to the Present Invention.

Figure 6:
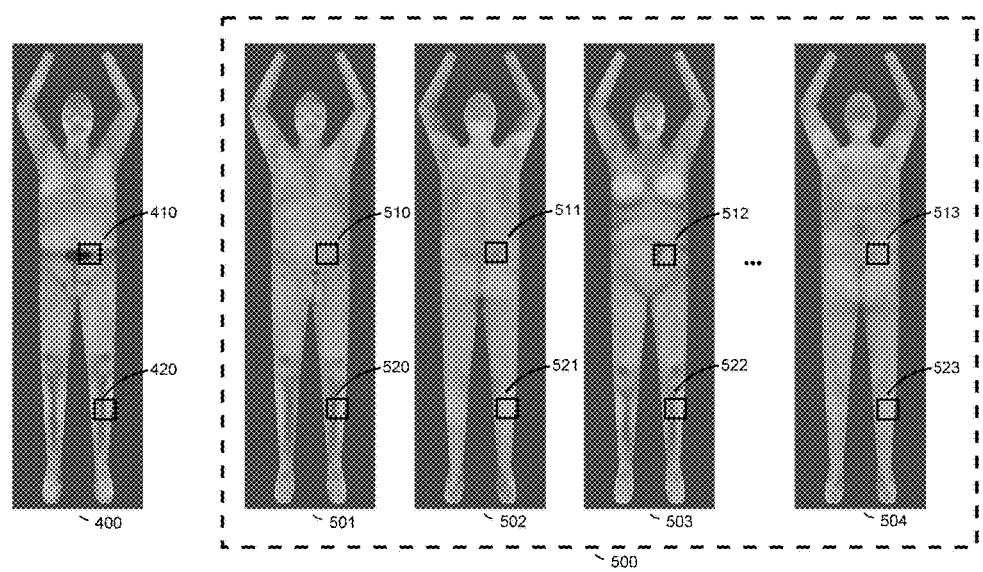
FIG. 6 is a depiction in accordance with the Present Invention.

As thus shown, any image 204 produced by the body scanner can be converted into an image 396 in humanoid coordinates. FIG. 6 is useful in explaining how this spatial conversion is used in the Present Invention to enable ATR. A number of images are acquired by operating the body scanner to scan persons with various body types. In a preferred embodiment this number is about 1,000 images, which is generally statistically sufficient to represent the population of all persons that will be searched with the body scanner. Each of these images is converted to humanoid coordinates. These converted images 501 502 503 504 form a reference database of images 500, which is stored in memory accessible to the computer for later access. Subsequently, the person being searched is scanned with the body scanner, and the resulting image converted to a subject scan 400 in humanoid coordinates. An image feature or region-of-interest is identified in the subject scan 400, such as the shin 420. This exemplary region 420 is then compared with the corresponding regions 520 521 522 523 in each of the database images 501 502 503 504, respectively. This comparison is accomplished by algorithms known in the art, such as numerically comparing brightness, edge sharpness, texture, and spectral composition. The result of this comparison is a numerical measure of how typical or common the feature or region of interest is in the database. If the numerical measure indicates it is common, such as in this example of the shin 420, the feature or region-of-interest is deemed to be resulting from anatomy or common benign objects. Therefore, it is removed from further consideration. As a converse example, the dark object in the belt region 410 in the scanned image is compared against the corresponding regions 510, 511 512 513 in the database images 501 502 503 504. This image pattern does not appear in the database, and would therefore be reported as uncommon by the comparison algorithms. Conversely, the metal object in the belt region would be classified as uncommon, and would remain for further security action.

In one embodiment, the feature under consideration in the scanned image is sequentially compared against the corresponding locations in each image in the reference database. This procedure determines the fraction of images in the database that reasonably contain the feature. For example, the feature of the shin 420 is reasonably matched in two of the database regions 520 522, and not matched in the remaining two regions 521 523. Therefore, this feature is contained in 50% of the database images. In the second example, the metal object on the belt feature 410 is contained in none of the corresponding regions in the database 510 511 512 513. Simply thresholding this frequency of occurrence parameter therefore results in the shin 420 being classified as not a threat, while the metal object on the belt 410 is classified as a threat.

In a preferred embodiment, the database scans are consolidated into a statistical representation to facilitate their comparison to the subject scan. As an example, the image feature being evaluated may be the grayscale value of each individual pixel in the subject image. In images created by backscatter x-ray body scanners, for example, dark pixels may indicate the presence of metal objects, while bright pixels may indicate the presence of explosives. However, ATR cannot be achieved by simply thresholding the subject scan for dark or bright pixels, since the normal variations in the human body also result in pixels that are dark and bright. In this embodiment, all of the images in the database are analyzed to find the mean pixel brightness, and the standard deviation of the pixel brightness, at each location in the humanoid coordinates. Further, this may be formatted as two grayscale images, where each pixel value in the first image is the mean, and each pixel value in the second image is the standard deviation. In this manner the multitude of images in the database are consolidated into only two images, which contain the key information for comparing the parameter of image brightness.

This consolidation of the database into mean and standard deviation images has the further advantage of allowing the ATR algorithms to be described as array processing, rather than pixel-by-pixel operations. In a preferred embodiment, a "standard deviation above the mean" (SDAM) image is created by subtracting the mean image from the subject image, and dividing the result by the standard deviation image. As known in the art of array processing, this defines that all pixels in the images are processed in the indicated manner. Each pixel value in the SDAM image is therefore a statistical measure of the typicality of the grayscale value at this location in the subject scan image, taken in comparison to the database scans. That is, for example, a value of −3 at a particular location in the SDAM image would indicate that the corresponding location in the subject image is exceedingly dark, three standard deviations below the mean in brightness, compared to the database images. As known in statistics, a numerical value more than three standard deviations from the mean occurs in only about 1 in 300 random occurrences. Therefore, this pixel value in the subject image would be highly uncommon, and indicative of a metal object. Likewise, a value of +3 would be exceedingly bright, three standard deviations above the mean, and indicative of explosive material. Pixel values in SDAM between about −2 and 2 are exceedingly common, and can immediately be dismissed from consideration. Again using array processing terminology, ATR detection of metal threats is accomplished by thresholding the SDAM image for values below a specified threshold, typically −2 to −5. Likewise, ATR detection of explosives is accomplished by thresholding the SDAM image for values above a specified threshold, typically 2 to 5.

In an analogous manner, a preferred embodiment of the Present Invention calculates and thresholds SDAM images for a variety of other features besides pixel brightness. This is essentially equivalent to consolidating the reference database in different fashions to facilitate specific comparisons. For instance, this includes edge sharpness, which can be calculated at each point in the subject image as the magnitude of the image gradient. Extended further, separate SDAM images of edge sharpness may be generated and evaluated for different edge angles. Further, the consolidation of the reference database may provide separation according to the sex of the subject, if the scan is a front or rear view of the subject, the subject's body type, and so on. Those skilled in the art will recognize that these are specific embodiments of comparing features in the subject scan with the database scans to identify those features that are uncommon.

Figure 7:
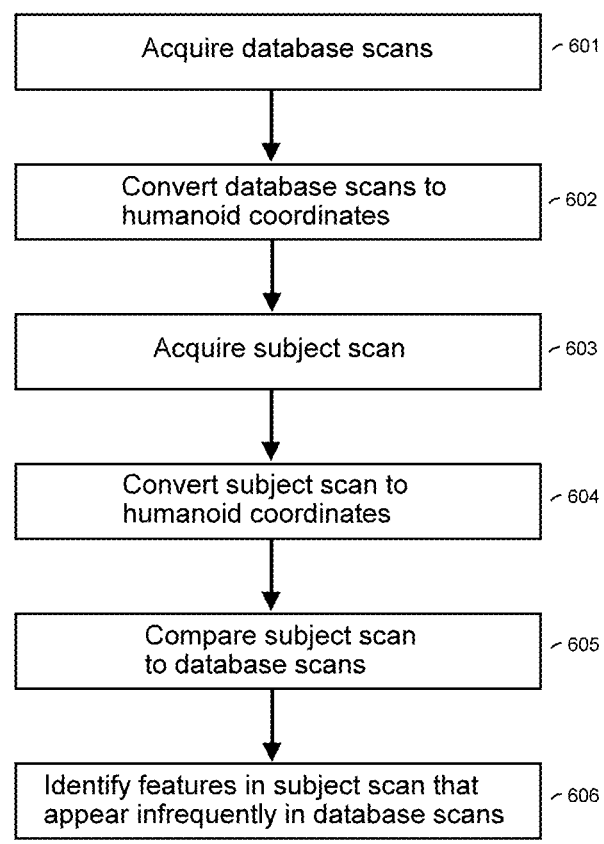
FIG. 7 is a depiction in accordance with the Present Invention.

FIG. 7 shows a preferred embodiment of the Present Invention in flowchart form. The first step 601 is to scan a number of persons with a body scanner to generate a database of scanned images. This number is typically 1,000, as needed to capture the body characteristics of the population of persons that will be screened using the Present Invention. The second step 602 is to convert the images in this database into humanoid coordinates. This preserves the image information about concealed objects, while eliminating interfering information resulting from different body types and different body postures. In a preferred embodiment this step is carried out by image warping, matching the outline and fiducial location on each scanned image to those of the humanoid coordinates, followed by the bilinear or similar image mapping transform. The third step 603 is to acquire a subject scan of the person being searched. The fourth step 604 is to convert the subject scan to humanoid coordinates, using the same procedure as in step 2 602. The fifth step 605 is to compare the subject scan, in humanoid coordinates, to the database scans, also in humanoid coordinates. In a preferred embodiment this comparison comprises numerical comparison of image features in the subject scan against the corresponding image locations in the database scans. The sixth step 606 is to identify features in the subject scan that do not commonly appear in the database scans. In a preferred embodiment this is indicated by atypical values of the numerical comparison. These identified features can therefore not be attributed to normal human anatomy nor common benign objects on the person, such as buttons, zippers, and jewelry. Accordingly, they are classified as abnormal, and indicative of a concealed threat.

As thus described, the images from the body scanner are converted into humanoid coordinates to facilitate the comparison of image features between images. This can be carried out by converting the entire scanned image into humanoid coordinates, and subsequently performing the feature detection and comparison operations on the converted data. In another preferred embodiment the feature detection is performed before the conversion operation. That is, features such as edges and brightness variations are identified in the image produced by the body scanner. The location of these features is then converted into humanoid coordinates, thereby enabling the comparison of these features between images. That is, the order of operations can be reversed, while still achieving the same result.

Although particular embodiments of the Present Invention have been described in detail for the purpose of illustration, various other modifications may be made without departing from the spirit and scope of the Invention. Different methods for identifying the outline of the body and fiducial location may be used. Likewise, different digital image warping techniques may be used to convert the images to humanoid coordinates. The format of the humanoid coordinates may be in other image and non-image formats. The reference database may be stored in other formats or statistical consolidations. The data representations at the various steps in the embodiments may be discrete, such as pixel values in a digital image, or mathematical, such as equations representing curves, or mathematical interpolations between discrete values. The computational platform to carry out the algorithms of the Present Invention may be a conventional sequential instruction computer, or a parallel hardware device such as an FPGA. The Present Invention may be used in conjunction with complementary ATR algorithms such as asymmetry detection and neural networks.

I claim:

1. A method for performing automated target recognition using a body scanner, comprising:
   acquiring database scans;
   converting said database scans to humanoid coordinates;
   acquiring subject scan;
   converting said subject scan to said humanoid coordinates;
   comparing converted subject scan to converted database scans; and
   identifying features in said converted subject scan that occur outside a threshold in said converted database scans.

2. The method of claim 1 wherein said comparing comprises consolidating said database scans into statistical representations.

3. The method of claim 1 wherein said features comprise image edges.

4. The method of claim 3 wherein said comparing comprises evaluating said image edges according to one or more of angle, location, and sharpness.

5. The method of claim 1 wherein said humanoid coordinates are derived from a body outline.

6. The method of claim 1 wherein said humanoid coordinates comprise a mapping from the coordinates of the database scans.

7. An apparatus for searching a person entering a security controlled area, comprising:
   a body scanner producing an electronic image of the person's body;
   a digital computer, said digital computer converting said electronic image into humanoid coordinates, and said digital computer comparing converted electronic image against a database to detect image features that occur outside a threshold in said converted electronic image;
   said converted electronic image and said database comprising said humanoid coordinates, wherein said humanoid coordinates represent a spatial frame-of-reference matched to the human body; and
   an annunciator responsive to the detection of said detected image features that occur outside a threshold.

8. The apparatus of claim 7 wherein said body scanner examines said person with backscatter and transmission x-ray radiation.

9. The apparatus of claim 7 wherein said spatial frame-of-reference matched to the human body is derived from an outline of said person's body.

10. The apparatus of claim 7 wherein said database comprises a plurality of images representative of human bodies.

11. The apparatus of claim 7 wherein said database comprises a statistical representation of different human body types.

12. The apparatus of claim 7 wherein said detected image features comprise edges.

13. A method for detecting security threats on a person, comprising:
   producing a database, said database comprising common features of the human body;
   converting said database into humanoid coordinates;
   producing a subject image, said subject image comprising features of the person's body;
   converting said subject image into humanoid coordinates; and
   comparing converted subject image against converted database.

14. The method of claim 13 wherein said humanoid coordinates are derived from bilateral fiducials.

15. The method of claim 13 wherein said humanoid coordinates comprise a body outline.

16. The method of claim 13 wherein said comparing comprises an image warping between scanner coordinates and said humanoid coordinates.

17. The method of claim 13 wherein said database comprises a statistical mean and a standard deviation of said common features of a human body.

18. The method of claim 17 wherein said common features of a human body comprise edges.

* * * * *